United States Patent
Sun et al.

(10) Patent No.: US 7,394,921 B2
(45) Date of Patent: Jul. 1, 2008

(54) INTEGRATED REGISTRATION OF DYNAMIC RENAL PERFUSION MAGNETIC RESONANCE IMAGES

(75) Inventors: Ying Sun, Plainsboro, NJ (US); Marie-Pierre Jolly, Hillsborough, NJ (US); José M. F. Moura, Pittsburgh, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 607 days.

(21) Appl. No.: 11/078,037

(22) Filed: Mar. 11, 2005

(65) Prior Publication Data
US 2005/0201601 A1    Sep. 15, 2005

Related U.S. Application Data
(60) Provisional application No. 60/553,364, filed on Mar. 15, 2004.

(51) Int. Cl.
*G06K 9/00* (2006.01)
(52) U.S. Cl. .................. 382/128; 382/173; 382/294
(58) Field of Classification Search ............. 382/128, 382/132, 173, 294
See application file for complete search history.

(56) References Cited

U.S. PATENT DOCUMENTS

| | | | | |
|---|---|---|---|---|
| 5,850,486 A | * | 12/1998 | Maas et al. | 382/294 |
| 6,718,055 B1 | * | 4/2004 | Suri | 382/128 |
| 7,020,311 B2 | * | 3/2006 | Breeuwer | 382/128 |

* cited by examiner

*Primary Examiner*—Tom Y Lu (57) ABSTRACT

A system and method are provided for integrated registration of images, the system including a processor, a first registration portion for performing rough registration of an image, a first segmentation portion for performing segmentation of an object of interest in the image, a second registration portion for performing fine registration of the image, and a second segmentation portion for performing segmentation of structures of the object of interest in the image; and the method including receiving a sequence of images, selecting an image from the sequence, cropping a region of interest (ROI) from the selected image, performing rough registration of the cropped ROI, performing segmentation of an object of interest from the rough registered ROI, performing fine registration of the ROI, and performing segmentation of structures of the object of interest from the fine registered ROI.

21 Claims, 6 Drawing Sheets

FIG. 6

INTEGRATED REGISTRATION OF DYNAMIC RENAL PERFUSION MAGNETIC RESONANCE IMAGES

CROSS-REFERENCE TO RELATED APPLICATION

This application claims the benefit of U.S. Provisional Application Ser. No. 60/553,364, filed Mar. 15, 2004 and entitled "Integrated Registration of Dynamic Renal Perfusion MR Images", which is incorporated herein by reference in its entirety.

BACKGROUND

Magnetic resonance (MR) imaging (MRI) has been used for the assessment of renal perfusion. In renal perfusion MRI, the abdomen is scanned rapidly and repeatedly following a bolus injection of a contrast agent. The kinematics of the contrast agent are reflected in the intensity changes of the obtained time series of MR images. Analysis of the dynamic behavior of the signal intensity can provide valuable functional information.

Unfortunately, a perfusion MR image sequence often suffers from motion induced by breathing during acquisition. To ensure the correspondence of anatomical structures in different time frames, registration of time-series images is necessary.

The registration of time-series images is a challenging task because the appearance of the kidney changes rapidly over the course of contrast enhancement, and therefore it is not accurate to use the common approach of block matching and looking for a best match in intensities across frames. In addition, different renal tissue types do not enhance uniformly, which results in a rapidly changing image contrast.

There has been limited work on the registration of dynamic renal perfusion MR images. An image processing system was proposed to correct organ displacements using model-based segmentation. A phase difference movement detection method and a semi-automatic contour registration method were also proposed. These methods all start with a manually drawn kidney contour in one time frame. That initial contour is used to obtain a mask or a model, and then it is propagated to other images in the sequence.

Accordingly, what is desired is an integrated image registration algorithm to correct the motion induced by patient breathing for dynamic renal perfusion MR images.

SUMMARY

These and other drawbacks and disadvantages of the prior art are addressed by an exemplary system and method for Integrated Registration of Dynamic Renal Perfusion Magnetic Resonance Images.

An exemplary system for integrated registration of images includes a processor, a first registration portion in signal communication with the processor for performing rough registration of at least one image, a first segmentation portion in signal communication with the processor for performing segmentation of an object of interest in the at least one image, a second registration portion in signal communication with the processor for performing fine registration of the at least one image, and a second segmentation portion in signal communication with the processor for performing segmentation of structures of the object of interest in the at least one image.

A corresponding exemplary method for integrated registration of images includes receiving a sequence of images, selecting an image from the sequence, cropping a region of interest (ROI) from the selected image, performing rough registration of the cropped ROI, performing segmentation of an object of interest from the rough registered ROI, performing fine registration of the ROI, and performing segmentation of structures of the object of interest from the fine registered ROI.

These and other aspects, features and advantages of the present disclosure will become apparent from the following description of exemplary embodiments, which is to be read in connection with the accompanying drawings.

BRIEF DESCRIPTION OF THE DRAWINGS

The present disclosure teaches a system and method for Integrated Registration of Dynamic Renal Perfusion Magnetic Resonance Images in accordance with the following exemplary figures, in which.

DETAILED DESCRIPTION OF PREFERRED EMBODIMENTS

An integrated image registration system and method are provided to correct the motion induced by patient breathing for dynamic renal perfusion magnetic resonance (MR) images. Registration of kidneys through the MR image sequence is a challenging task due to rapidly changing image contrast over the course of contrast enhancement.

An exemplary algorithm embodiment achieves temporal image registration in a multi-step fashion. The embodiment roughly registers the images by detecting large-scale motion, and then refines the registration results by integrating region information and local gradient information with auxiliary image segmentation results. The exemplary embodiment has obtained excellent registration results for several real patients.

In the exemplary integrated image registration algorithm, a user may crop a rectangular region of interest (ROI) containing a kidney. Large-scale motion is identified by maximizing an edge-based consistency metric that is invariant to rapidly changing contrast, and the registration results are refined by integrating region information and edge information with auxiliary image segmentation results. By exploiting the invariance of the consistency metric, this algorithm can successfully identify the translational motion of the kidney across the image sequence.

Figure 1:
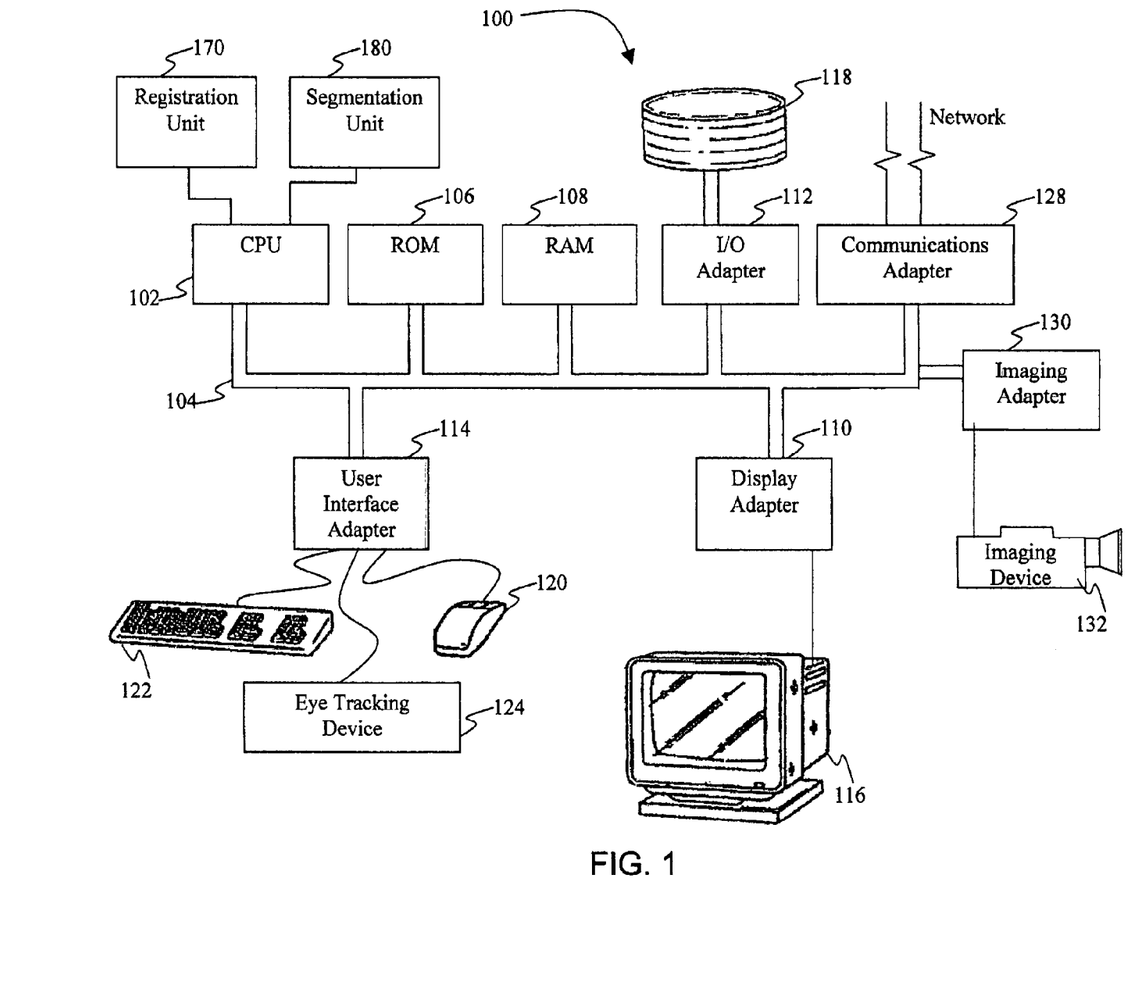
FIG. 1 shows a schematic diagram of a system for Integrated Registration of Dynamic Renal Perfusion Magnetic Resonance Images in accordance with an illustrative embodiment of the present disclosure.

As shown in FIG. 1, a system for Integrated Registration of Dynamic Renal Perfusion Magnetic Resonance Images, according to an illustrative embodiment of the present disclosure, is indicated generally by the reference numeral 100. The system 100 includes at least one processor or central processing unit (CPU) 102 in signal communication with a system bus 104. A read only memory (ROM) 106, a random access memory (RAM) 108, a display adapter 110, an I/O adapter 112, a user interface adapter 114, a communications adapter 128, and an imaging adapter 130 are also in signal communication with the system bus 104. A display unit 116 is in signal communication with the system bus 104 via the display adapter 110. A disk storage unit 118, such as, for example, a magnetic or optical disk storage unit is in signal communication with the system bus 104 via the I/O adapter 112. A mouse 120, a keyboard 122, and an eye tracking device 124 are in signal communication with the system bus 104 via the user interface adapter 114. An imaging device 132 is in signal communication with the system bus 104 via the imaging adapter 130.

A registration unit 170 and a segmentation unit 180 are also included in the system 100 and in signal communication with the CPU 102 and the system bus 104. While the registration unit 170 and the segmentation unit 180 are illustrated as coupled to the at least one processor or CPU 102, these components are preferably embodied in computer program code stored in at least one of the memories 106, 108 and 118, wherein the computer program code is executed by the CPU 102.

Figure 2:
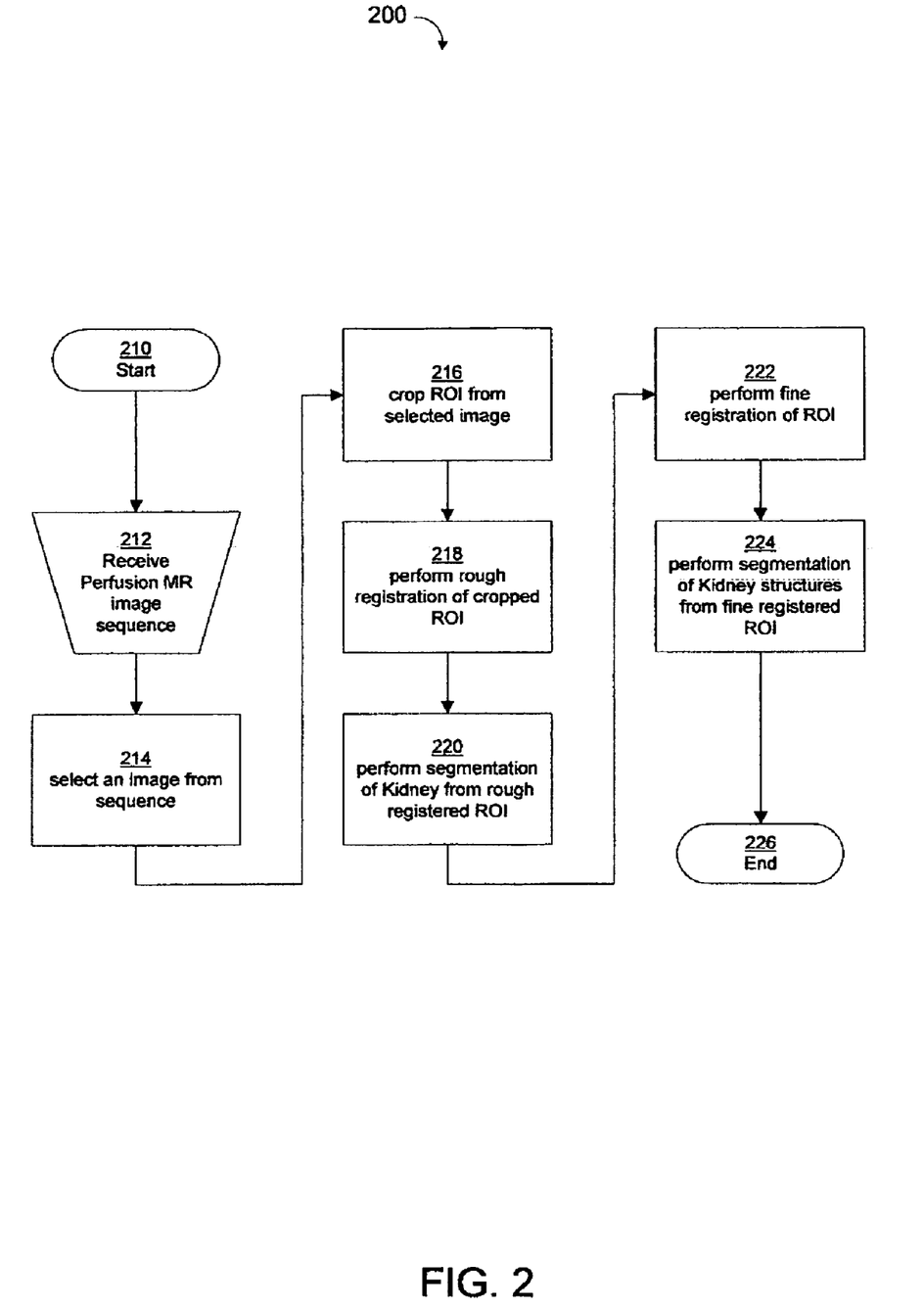
FIG. 2 shows a flow diagram of a method for Integrated Registration of Dynamic Renal Perfusion Magnetic Resonance Images in accordance with an illustrative embodiment of the present disclosure.

Turning to FIG. 2, a method for Integrated Registration of Dynamic Renal Perfusion Magnetic Resonance Images, according to an illustrative embodiment of the present disclosure, is indicated generally by the reference numeral 200. The method 200 includes a start block 210 that passes control to an input block 212. The input block 212 receives a sequence of perfusion magnetic resonance images, and passes control to a function block 214. The function block 214 selects an image from the sequence and passes control to a function block 216. The function block 216 crops a region of interest (ROI) from the selected image, and passes control to a function block 218. The function block 218 performs a rough registration of the cropped ROI, and passes control to a function block 220.

The function block 220, in turn, performs a segmentation of a kidney from the rough registered ROI, and passes control to a function block 222. The function block 222 performs a fine registration of the ROI, and passes control to a function block 224. The function block 224 performs segmentation of kidney structures from the fine registered ROI, and passes control to an end block 226.

Figure 3:
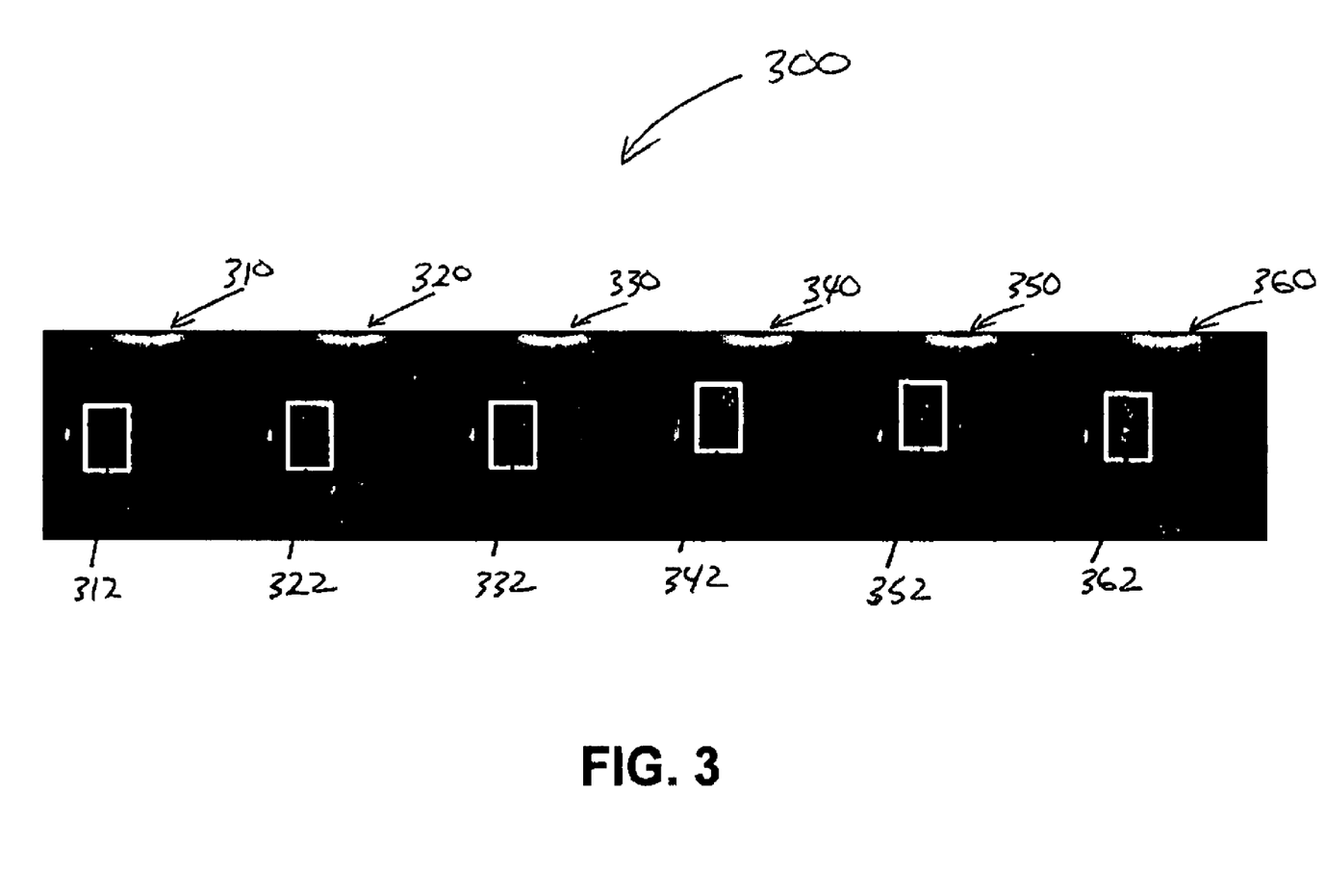
FIG. 3 shows graphical image diagrams for rough registration results of representative images selected from a dynamic renal perfusion MR image sequence in accordance with an illustrative embodiment of the present disclosure.

Turning now to FIG. 3, representative images sampled from a renal perfusion sequence are indicated generally by the reference numeral 300. The representative images 310, 320, 330, 340, 350 and 360, respectively, are in chronological order. Results obtained using the exemplary method are superimposed by shifting the respective bounding boxes 312, 322, 332, 342, 352 and 362 to the best match location in each image. As shown, the intensity of the kidney increases as the contrast agent perfuses into the cortex, the medulla, and other structures of the kidney.

Figure 4:
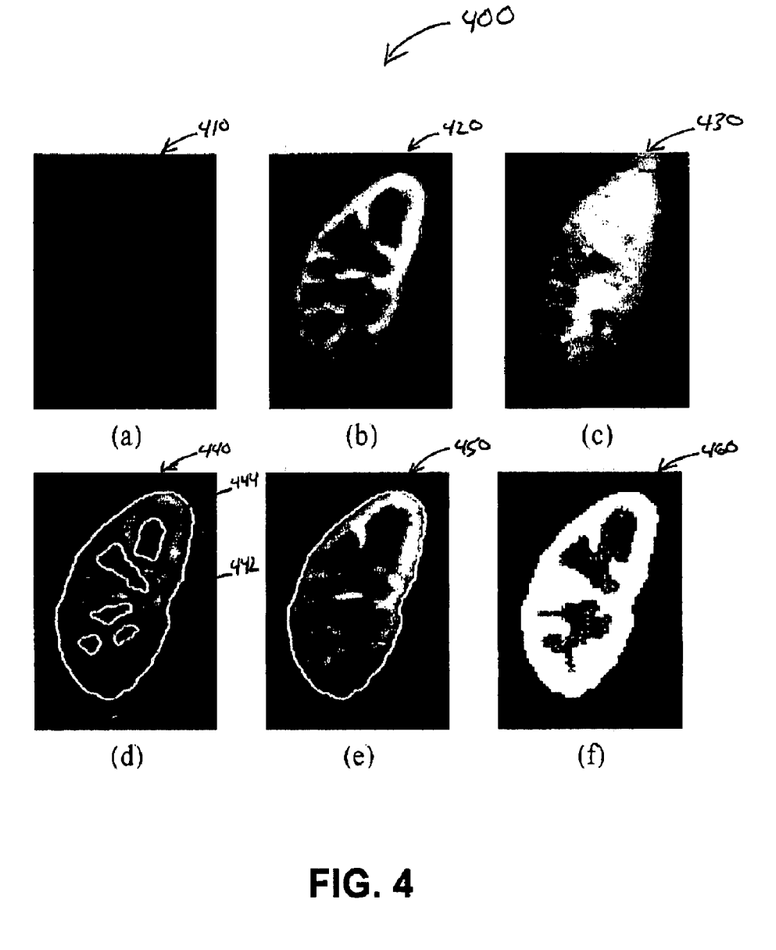
FIG. 4 shows graphical image diagrams for segmentation results of roughly registered images in accordance with an illustrative embodiment of the present disclosure.

As shown in FIG. 4, registered region of interest (ROI) images are indicated generally by the reference numeral 400. The images 410, 420 and 430 represent pre-contrast, wash-in, and post-contrast, respectively, during a perfusion process. Based on each individual image, it is difficult to distinguish different anatomical structures due to the lack of contrast along some boundary segments. However, subtracting the pre-contrast image 410 from the high-contrast wash-in image 420 results in the enhanced image 440. The enhanced subtraction image 440 includes contours 442 and 444. Final segmentation results from overlaying contours on an original image from the sequence are shown in the image 450, while the image 460 displays the mask for the renal cortex.

Figure 5:
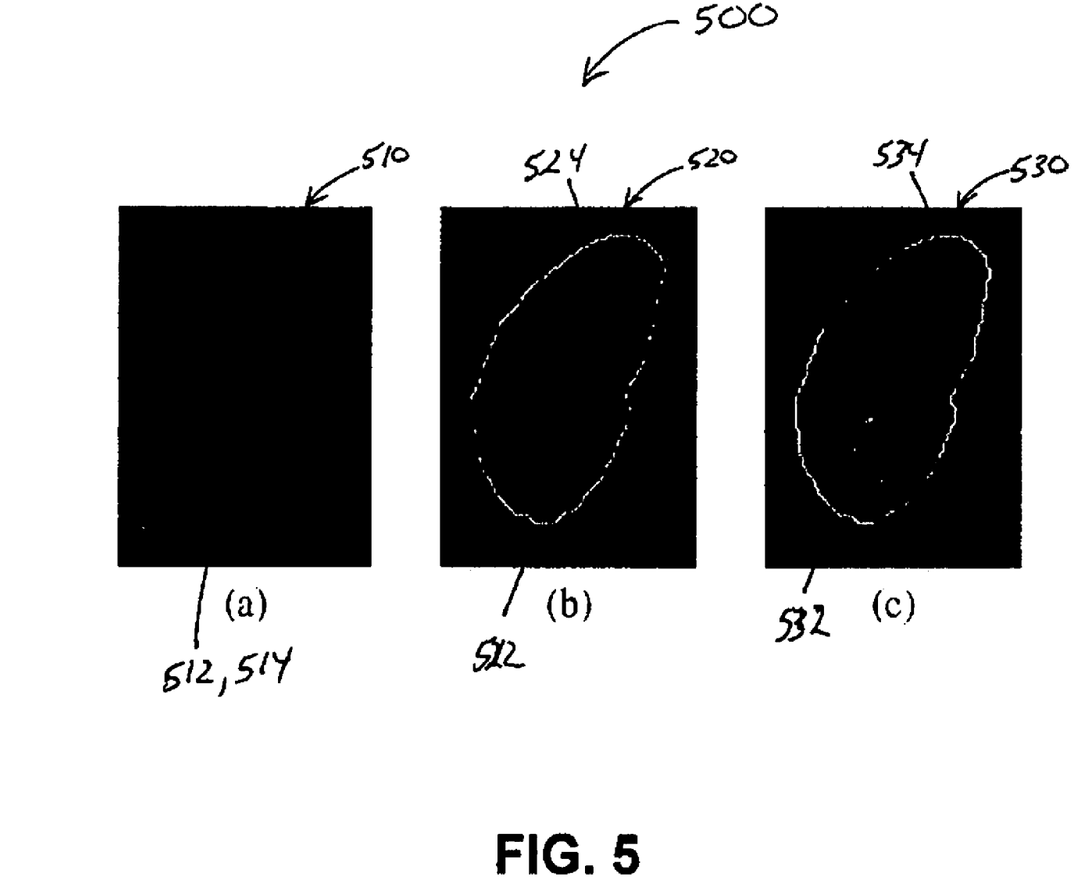
FIG. 5 shows graphical image diagrams of fine registration for accuracy improvement in accordance with an illustrative embodiment of the present disclosure.

Turning to FIG. 5, additional registered ROI images are indicated generally by the reference numeral 500. In the image 510, a thick contour 512 is identical to a thin contour 514. For the other images 520 and 530, the thick contours 522 and 532, respectively, delineate the kidney boundary more accurately than the thin contours 524 and 534, respectively.

Figure 6:
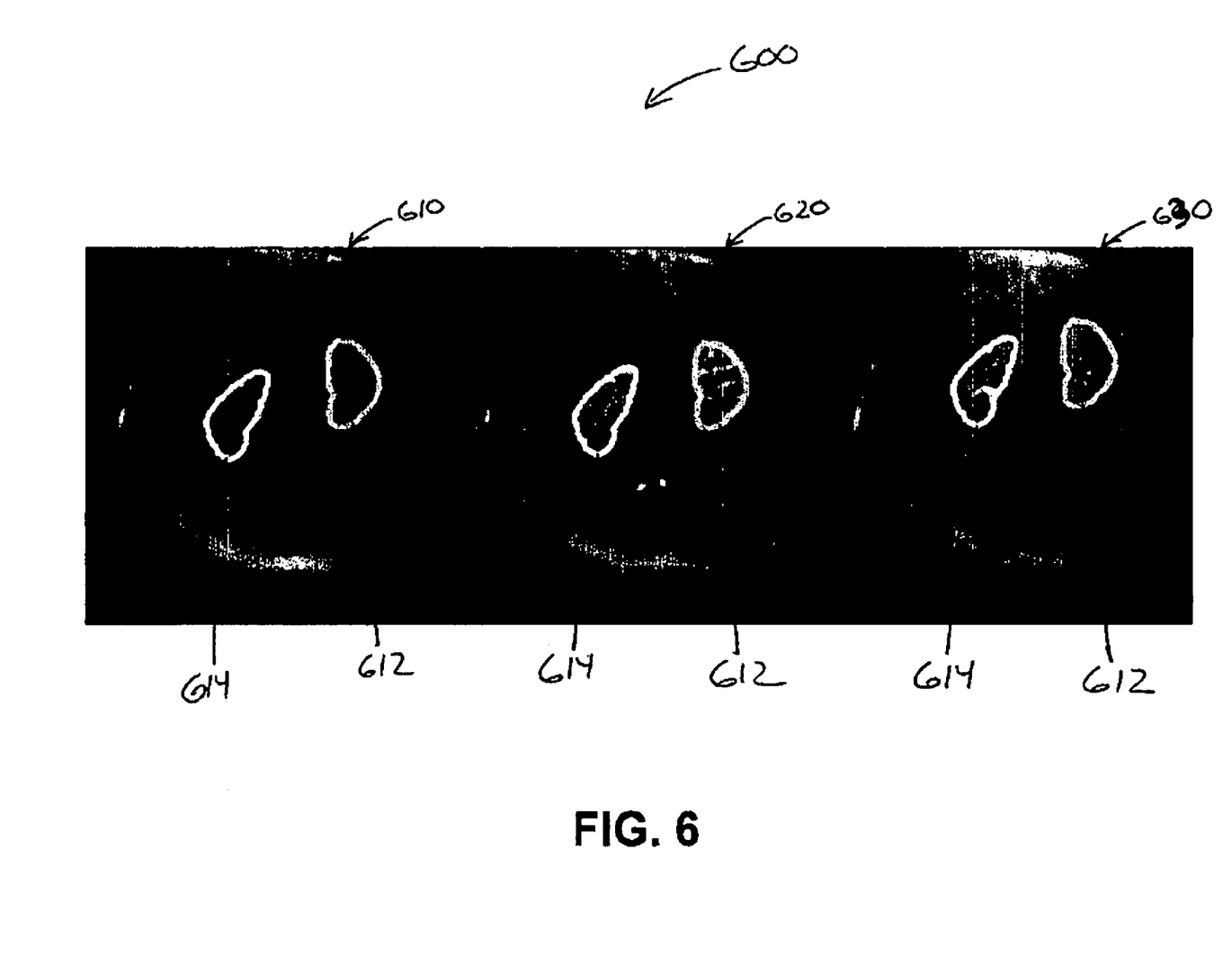
FIG. 6 shows graphical image diagrams of results obtained using the integrated registration algorithm on a real patient MR perfusion sequence for both kidneys in accordance with an illustrative embodiment of the present disclosure.

Turning now to FIG. 6, image results obtained using the integrated registration algorithm on a real patient MR perfusion sequence for both kidneys are indicated generally by the reference numeral 600. The images 610, 620 and 630 are in chronological order before, during, and after contrast enhancement, respectively, to illustrate the performance of the exemplary algorithm for a real patient. The algorithm was performed separately for the left kidney 612 and the right kidney 614. As shown, the exemplary algorithm successfully identified the boundaries, shown here as solid contours, of both kidneys in all of the images acquired before, during, and after contrast enhancement.

In operation, an exemplary integrated image registration algorithm uses the interdependence between segmentation and registration. Registration and segmentation are mutually beneficial. Segmentation helps registration in that informative features in the images can be identified based on segmentation results. These features are required by a large class of image registration methods prior to the registration process. On the other hand, successful registration enables the use of the entire sequence of images in the segmentation.

Referring back to FIG. 2, a multi-step approach is used in which segmentation and registration are interleaved. The user may crop a ROI containing one kidney in a single high-contrast image. First, the method roughly registers the selected ROI across the image sequence. Then, it obtains the contours that delineate the boundaries of renal cortex, by segmenting the subtraction image between the high-contrast image and a pre-contrast image. Next, it propagates these contours to other images in the sequence with integer pixel shifts. Finally, the entire image sequence is used to segment different anatomical structures.

To formulate the rough registration problem, two assumptions are made. First, it is assumed that the kidney is a rigid body, and thus, its shape does not change during the perfusion process. Second, it is assumed that the motion is only translational while ignoring possible scaling and rotation induced by out-of-plane motion. This is a reasonable assumption because translation is the dominant motion. Given a rectangular ROI in one frame, the goal of this module is to find the best match in other time frames by shifting the bounding box of the selected ROI with integer pixel offsets. In this exemplary approach, rough registration is accomplished by template matching.

For template matching, it is important to extract the right features to build the template. Generally two channels of information are used, the intensity and the local gradient. In this case, the intensity changes rapidly and one does not know exactly which intensity level the template should assume. Here, image features invariant to rapid intensity and contrast changes are used. Although the relative intensities between tissues vary with time, it is observed that the orientations of the edges along tissue boundaries are always parallel across the image sequence. Thus, the template defined by the image gradient is chosen.

In this formulation, the image on which the ROI is manually cropped is called the reference image. Let $(x_l^r, y_l^r)$ be the position of the $l^{th}$ pixel inside the ROI. Let $\theta_l^r$ and $M_l^r$ stand for respectively the direction and magnitude of the image gradient at the corresponding pixel in the reference image; one can obtain $\theta_l^r$ and $M_l^r$ using a Sobel edge detector. It has been experimentally observed that the final registration results are basically insensitive to the choice of edge detector. Let $S=\{1,2,\ldots,L\}$ denote the set of indices of all the pixels inside the ROI, the template is represented by a set of four tuples $\{(x_l^r, y_l^r, \theta_l^r, M_l^r) | l \in S\}$. Let $\theta_c(x,y)$ denote the edge orientation and $M_c(x,y)$ the edge magnitude at pixel $(x,y)$ in the current image; an edge-based consistency metric for each pair of offsets $(dx,dy)$ is defined as follows.

$$C(dx, dy) = \frac{\sum_{l=1}^{L} [w_l(dx, dy)\cos(2\Delta\theta_l(dx, dy))]}{\sum_{l=1}^{L} w_l(dx, dy)}, \quad (1)$$

where $w_l(dx,dy)$ and $\Delta\theta_l(dx,dy)$ are the weight and the angle difference, respectively.

$$w_l(dx, dy) = M_c(x_l^r + dx, y_l^r + dy) M_l^r \quad (2)$$

$$\Delta\theta_l(dx, dy) = \theta_c(x_l^r + dx, y_l^r + dy) - \theta_l^r \quad (3)$$

This is a weighted sum of $\cos(2\Delta\theta)$ over the ROI. The cosine of the double angle difference between the current edge orientation and the reference orientation is chosen for two reasons. First, it is invariant to contrast change, i.e., the angle difference between an edge defined by a transition from dark to bright and by a transition from bright to dark is $\Delta\theta=\pi$, which results in $\cos(2\pi)=\cos(0)$. Second, it is a nonlinear function whose first order derivative peaks at $\Delta\theta=\pm\pi/4$, which makes its value relatively less sensitive to disturbances around $\Delta\theta=0,\pi/2$. Furthermore, the product of the edge magnitudes is used as weight because it is desirable for the ROI to be attracted to strong edges whose orientations are consistent with those of the template. To summarize, using the proposed consistency metric overcomes problems related to the variation in the image contrast.

Since the location of the kidney is confined to a certain range, one only needs to compute $C(dx,dy)$ within a searching window. The integer shifts $(dx^*,dy^*)$ that maximize C are determined by exploring all possible solutions $(dx,dy)$ over the search space. Although this is an exhaustive search, it is still fast because the search space is limited, usually to 30×10.

Referring back to FIG. 3, it displays representative images sampled from a renal perfusion sequence. Results obtained using the proposed method are superimposed by shifting the bounding box to the best match location in each image. As shown, the intensity of the kidney increases as the contrast agent perfuses into the cortex, the medulla, and other structures of the kidney. Despite the rapidly changing contrast and the fact that translational motion of the kidney between two adjacent frames can be considerably large, the algorithm is able to track the kidney reliably in the complete sequence of 250 images, with a maximum tracking error less than 2 pixels in both directions. The tracking error arises in images that lack strong edges because only the edge information in the template is used. To improve the registration accuracy, the homogeneity of pixel intensities may be integrated with the edge information by incorporating the knowledge of the contour delineating the kidney boundary.

Segmentation of the kidney identifies the boundary of the kidney. Since the renal cortex is the outer layer of the kidney, one may obtain the kidney boundary by segmenting the cortex from the roughly registered image sequence. Referring back to FIG. 4, the first three registered ROI images represent pre-contrast, wash-in, and post-contrast, respectively, during a perfusion process. Based on each individual image, it is difficult to distinguish different anatomical structures due to the lack of contrast along some boundary segments. However, subtracting the pre-contrast image from the high-contrast wash-in image results in the enhanced fourth image 440. Thanks to the wash-in of the contrast agent, detecting the boundaries of the renal cortex becomes a less challenging problem, to which one can apply, for example, the level set method as known in the art.

The level set method is an energy minimization based segmentation method. It assumes that the image is formed by two regions of approximately piecewise constant intensities of distinct values. In our case, it can be seen easily in the image 440 of FIG. 4 that the assumption is valid; the image contains a bright object to be detected and a dark background.

The segmentation results obtained using the level set method are overlaid on the subtraction image 440. Here the dotted contours 442 are the initial curves, while the solid contours 444 are the resulting curves. Although this is an approximate segmentation of the renal cortex, the outer boundary of the kidney is well delineated. Utilization of other images in the sequence, such as the post-contrast image 430, leads to a more accurate segmentation of the renal cortex. The image 450 shows the final segmentation results by overlaying the contours on an original image from the sequence, while the image 460 displays the mask for the renal cortex. These results indicate that the kidney boundary is identified accurately and a mask is successfully obtained for the cortex.

Fine registration is performed next. The segmentation results obtained in the previous step make it possible to refine the template by ignoring irrelevant edge information, and at the same time, by incorporating regional homogeneity of pixel intensities. Recall that the old template described above is represented by $\{(x_l^r, y_l^r, \theta_l^r, M_l^r) | l \in S\}$. Let $S_i \subset S$ denote the set of indices corresponding to either edge pixels lying on the kidney boundary or their nearest neighbors under a second order neighborhood system. The edge-based consistency metric for the current image is then reduced to $$C_e(dx, dy) = \frac{\sum_{l \in S_1} [w_l(dx, dy)\cos(2\Delta\theta_l(dx, dy))]}{\sum_{l \in S_1} w_l(dx, dy)}, \quad (4)$$

Let $S_2 \subset S$ denote the set of N pixels that belong to the cortex mask. Let $$m_c(dx, dy) = \frac{1}{N} \sum_{l \in S_2} I(x_l^r + dx, y_l^r + dy)$$

represent the average pixel intensity over the cortex mask in the current image for offset(dx,dy). A region-based consistency metric is defined that penalizes intensity inhomogeneity as:

$$C_r(dx, dy) = \frac{1 - \kappa^2(dx, dy)}{1 + \kappa^2(dx, dy)}, \quad (5)$$

$$\kappa(dx, dy) = \frac{\sqrt{\frac{1}{N}\sum_{l \in S_2}[I(x_l^r + dx, y_l^r + dy) - m_c(dx, dy)]^2}}{m_c(dx, dy)}. \quad (6)$$

Note that κ is analogous to the tangent of an angle, which makes $C_r$ the cosine of the double angle like $C_e$. The above two metrics are combined as a weighted sum to obtain C'(dx, dy)=$\lambda_c$$C_e$(dx,dy)+(1-$\lambda_c$)$C_r$(dx,dy), where 0≦$\lambda_c$≦1, and the value of $\lambda_c$ is linearly proportional to the average gradient magnitude in the current image. Thus, edge information is dominant in images with strong edges. In contrast, region information plays a more important role in images without strong edges. The integer shifts can be determined by maximizing C'(dx,dy).

Referring back to FIG. 5, the images 510, 520 and 530 compare the results obtained before (shown by thin contours 512, 522, 532) and after (shown by thick contours 514, 524, 534) applying the fine registration algorithm. For some images, such as 510, the thick contour is identical to the thin contour; for other images, such as 520 and 530, the thick contours delineate the kidney boundary more accurately.

The exemplary algorithm was tested on five real patient perfusion data sets. Each data set contains four slices. The images were acquired on Siemens Sonata MR scanners following bolus injection of Gd-DTPA contrast agent. The image matrix was 256×256 pixels. The number of frames in each image sequence ranges from 150 to 350.

Referring back to FIG. 6, results are presented for a real patient to illustrate the performance of the exemplary algorithm. The algorithm was performed separately for the left and right kidneys, 612 and 614, respectively. As shown, it has successfully identified the boundaries, which are shown as solid contours, of both kidneys in all the images acquired before, during and after contrast enhancement.

For all of the data sets in the study, it is observed that the integer pixel shifts obtained using the exemplary algorithm are highly consistent with the actual shifts. The registration results have been quantitatively validated for one sequence of 150 images, by comparing the resulting integer pixel shifts with a "gold standard," i.e., pixel shifts obtained manually. An error size of at most one pixel is obtained for over 95% of the images.

Accordingly, an exemplary embodiment of the present disclosure is an integrated registration algorithm for dynamic renal perfusion MR images. The algorithm integrates region information and edge information with auxiliary image segmentation results. A strength of the algorithm is in the utilization of image features that are invariant to a rapidly changing contrast. Excellent results have been obtained with several real patient data sets. The algorithm disclosed herein for tracking translational integer pixel motion of the kidney may be used as the preprocessing step of a sub-pixel registration method. These registration results may be used to segment different kidney structures based on the distinct dynamics of their intensity-time curve. In the exemplary embodiment registration framework, the kidney is assumed to be a rigid body. Alternate embodiments may take into account out-of-plane motion by incorporating parameters for rotation and scaling.

In alternate embodiments of the apparatus 100, some or all of the computer program code may be stored in registers located on the processor chip 102. In addition, various alternate configurations and implementations of the registration unit 170 and the segmentation unit 180 may be made, as well as of the other elements of the system 100.

It is to be understood that the teachings of the present disclosure may be implemented in various forms of hardware, software, firmware, special purpose processors, or combinations thereof. Most preferably, the teachings of the present disclosure are implemented as a combination of hardware and software.

Moreover, the software is preferably implemented as an application program tangibly embodied on a program storage unit. The application program may be uploaded to, and executed by, a machine comprising any suitable architecture. Preferably, the machine is implemented on a computer platform having hardware such as one or more central processing units (CPU), a random access memory (RAM), and input/output (I/O) interfaces.

The computer platform may also include an operating system and microinstruction code. The various processes and functions described herein may be either part of the microinstruction code or part of the application program, or any combination thereof, which may be executed by a CPU. In addition, various other peripheral units may be connected to the computer platform such as an additional data storage unit and a printing unit.

It is to be further understood that, because some of the constituent system components and methods depicted in the accompanying drawings are preferably implemented in software, the actual connections between the system components or the process function blocks may differ depending upon the manner in which the present disclosure is programmed. Given the teachings herein, one of ordinary skill in the pertinent art will be able to contemplate these and similar implementations or configurations of the present disclosure.

Although the illustrative embodiments have been described herein with reference to the accompanying drawings, it is to be understood that the present disclosure is not limited to those precise embodiments, and that various changes and modifications may be effected therein by one of ordinary skill in the pertinent art without departing from the scope or spirit of the present disclosure. All such changes and modifications are intended to be included within the scope of the present disclosure as set forth in the appended claims.

What is claimed is:

1. A method for integrated registration of images, the method comprising:
   receiving a sequence of images;
   selecting an image from the sequence;
   cropping a region of interest (ROI) from the selected image;
   performing rough registration of the cropped ROI;
   performing segmentation of an object of interest from the rough registered ROI;
   performing fine registration of the ROI; and
   performing segmentation of structures of the object of interest from the fine registered ROI.

2. A method as defined in claim 1 wherein the images are dynamic renal perfusion magnetic resonance (MR) images.

3. A method as defined in claim 1 wherein the object of interest is a kidney.

4. A method as defined in claim 1 wherein the segmentation of an object is responsive to the rough registration.

5. A method as defined in claim 1 wherein the fine registration is responsive to at least one of the rough registration and the segmentation of an object.

6. A method as defined in claim 1 wherein each of the rough registration and the fine registration are temporal.

7. A method as defined in claim 1 wherein performing rough registration includes detecting large-scale motion.

8. A method as defined in claim 1 wherein performing fine registration includes integrating region information and local gradient information with auxiliary image segmentation results.

9. A method as defined in claim 1 wherein cropping the ROI containing the object of interest is user-controlled.

10. A method as defined in claim 1 wherein the ROI is rectangular.

11. A method as defined in claim 7 wherein large-scale motion is identified by maximizing an edge-based consistency metric that is invariant to rapidly changing contrast.

12. A method as defined in claim 1 wherein registration results are refined by integrating region information and edge information with auxiliary image segmentation results.

13. A method as defined in claim 11, further comprising identifying the translational motion of the object of interest across the image sequence by exploiting the invariance of the consistency metric.

14. A system for integrated registration of images, the system comprising:
    a processor;
    a first registration portion in signal communication with the processor for performing rough registration of at least one image;
    a first segmentation portion in signal communication with the processor for performing segmentation of an object of interest in the at least one image;
    a second registration portion in signal communication with the processor for performing fine registration of the at least one image; and
    a second segmentation portion in signal communication with the processor for performing segmentation of structures of the object of interest in the at least one image.

15. A system as defined in claim 14 wherein the second registration portion is in further signal communication with the first segmentation portion.

16. A system as defined in claim 14 wherein the second segmentation portion is in further signal communication with the second registration portion.

17. A system as defined in claim 14, further comprising a user interface adapter for cropping a region of interest (ROI) from the at least one image.

18. A computer-readable medium, tangibly embodying a program of instructions executable by a computer to perform program steps for integrated registration of images, the program steps comprising:
    receiving a sequence of images;
    selecting an image from the sequence;
    cropping a region of interest (ROI) from the selected image;
    performing rough registration of the cropped ROI;
    performing segmentation of an object of interest from the rough registered ROI;
    performing fine registration of the ROI; and
    performing segmentation of structures of the object of interest from the fine registered ROI.

19. A computer-readable medium as defined in claim 18 wherein the program step of performing rough registration includes detecting large-scale motion.

20. A computer-readable medium as defined in claim 19 wherein large-scale motion is identified by maximizing an edge-based consistency metric that is invariant to rapidly changing contrast.

21. A computer-readable medium as defined in claim 20, further comprising the program step of identifying the translational motion of the object of interest across the image sequence by exploiting the invariance of the consistency metric.

* * * * *